United States Patent
Passi et al.

(10) Patent No.: US 6,322,507 B1
(45) Date of Patent: Nov. 27, 2001

(54) ULTRASONIC APPARATUS AND METHOD FOR EVALUATION OF BONE TISSUE

(75) Inventors: Garri Passi, Ashdod; Shmuel Buksphan, Rehovot; Arcady Golden, Ashdod; Uriel Halavee, Ramat Gan; Gadi Keren, Kiriat Ono; Vladimir Moshkovich, Rishon Lezion, all of (IL)

(73) Assignee: Medson Ltd., Rehovot (IL)

( * ) Notice: Subject to any disclaimer, the term of this patent is extended or adjusted under 35 U.S.C. 154(b) by 0 days.

(21) Appl. No.: 09/445,411
(22) PCT Filed: Oct. 25, 1999
(86) PCT No.: PCT/IL99/00563
§ 371 Date: Dec. 8, 1999
§ 102(e) Date: Dec. 8, 1999
(87) PCT Pub. No.: WO00/24307
PCT Pub. Date: May 4, 2000

Related U.S. Application Data

(60) Provisional application No. 60/105,568, filed on Oct. 25, 1998.

(51) Int. Cl.[7] .................................................. A61B 8/00
(52) U.S. Cl. .................................... 600/437; 600/449
(58) Field of Search ............................ 600/437, 438, 600/442, 443, 449, 459; 310/336; 601/2; 73/597, 599, 602

(56) References Cited

U.S. PATENT DOCUMENTS 4,941,474 * 7/1990 Pratt, Jr. ............................. 600/437
5,143,069 * 9/1992 Kwon et al. ........................ 600/437
5,879,301 * 3/1999 Chiabrera et al. .................. 600/437

* cited by examiner

Primary Examiner—Marvin M. Lateef
Assistant Examiner—Ali M. Imam

(57) ABSTRACT

A method and system for ultrasonic imaging of bone tissue. A wide band scanning crystal transmits an ultrasonic signal of high frequency and multiple full waves into the bone tissue, and a second wide band scanning crystal receives the transmitted signal. The transmission frequency is progressively decreased until the number of full waves in the received signal equals that of the transmitted signal. At that frequency, the upper frequency limit, the number of full waves in the transmitted signal is gradually increased until the received signal contains at least two consecutive full waves of equal amplitude. The resultant transmission signal is then used to measure signal attenuation and velocity in bone tissue, in terms of standard bone imaging techniques. A lower frequency limit, below which the received signal undergoes distortion, is defined, and ultrasonic velocity depicted as a function of transmission frequency. Received ultrasonic wave frequency spectra, and the difference between the upper and lower frequency limits, are all used to image the bone tissue. Probe orientation is enhanced by a mechanism whereby a third wide band screening crystal receives the transmitted signal concomitantly with the second screening crystal. The signals received by the two wide band scanning crystals are correlated with each other to give a numerical indicator of the adequacy of probe orientation.

12 Claims, 19 Drawing Sheets

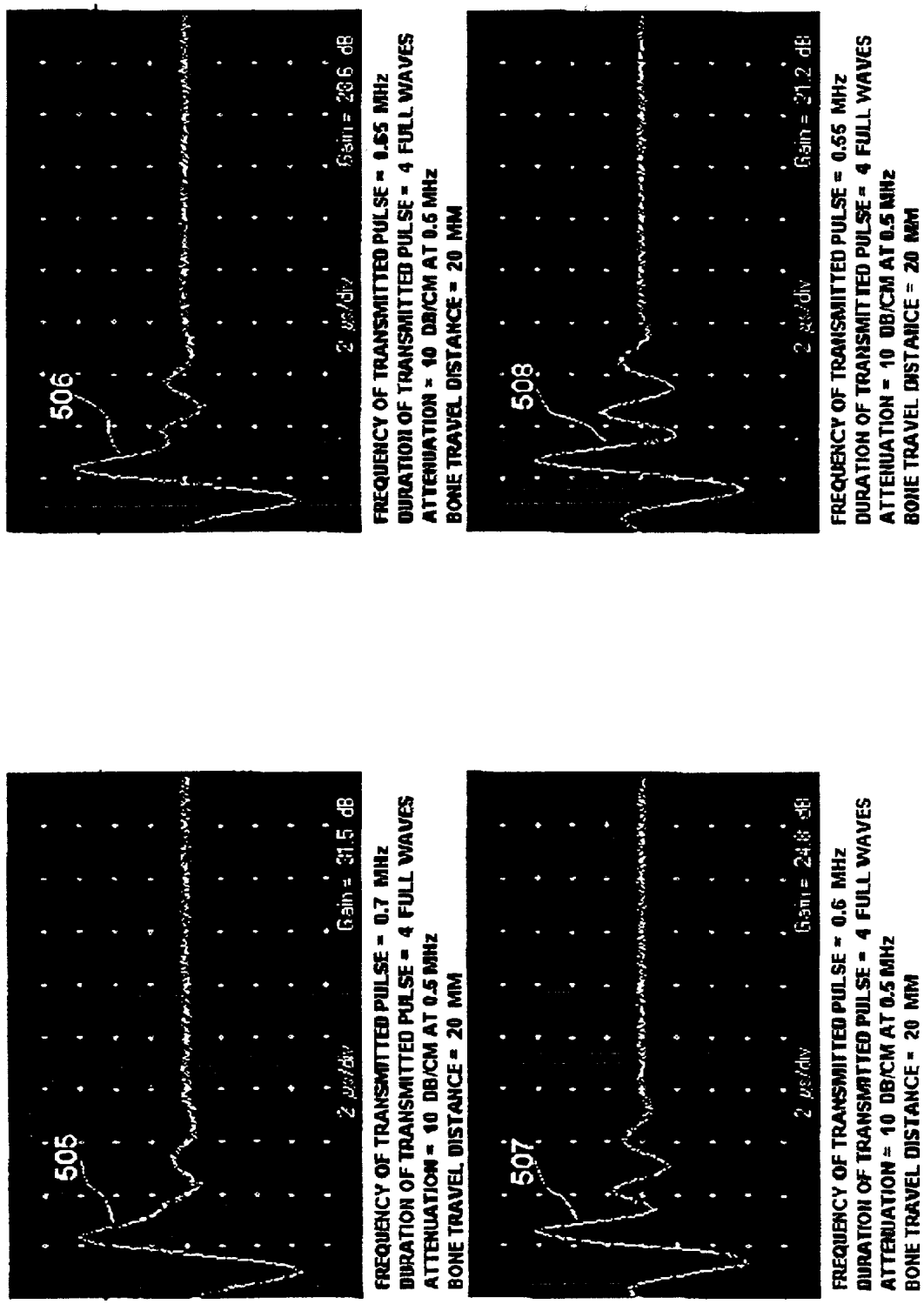
FIG.5 (CONTINUATION A)

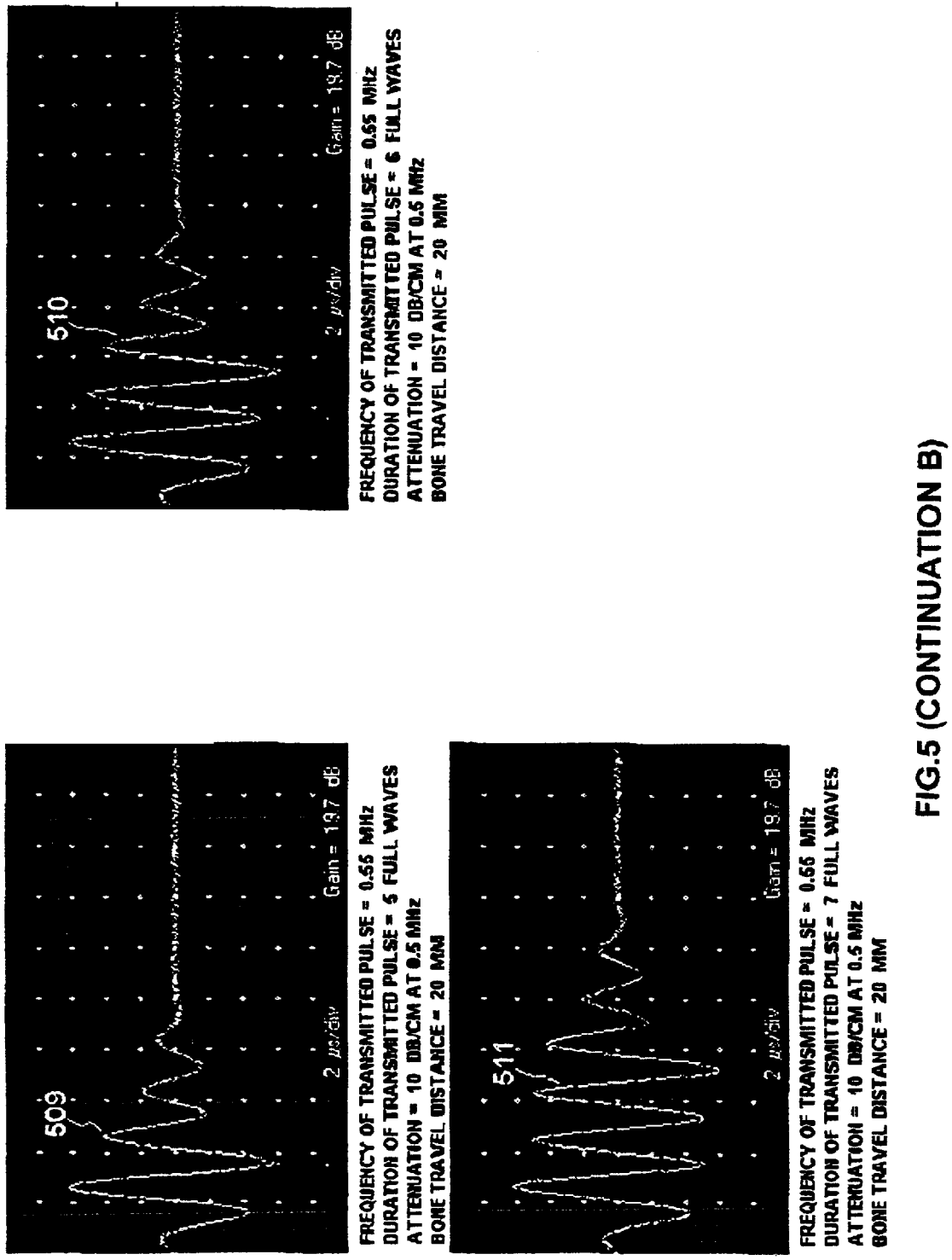
FIG.5 (CONTINUATION B)

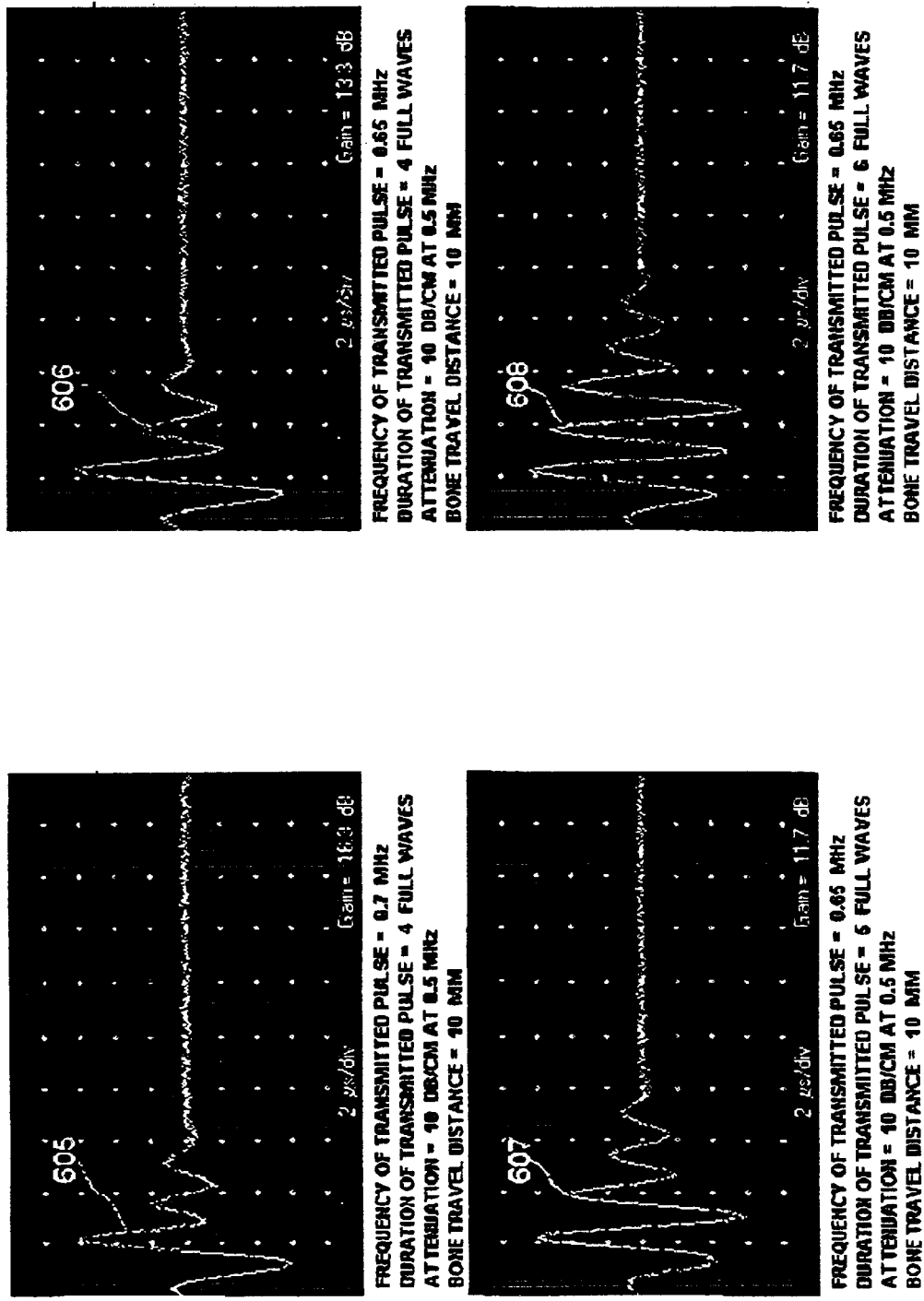
FIG.6 (CONTINUATION A)

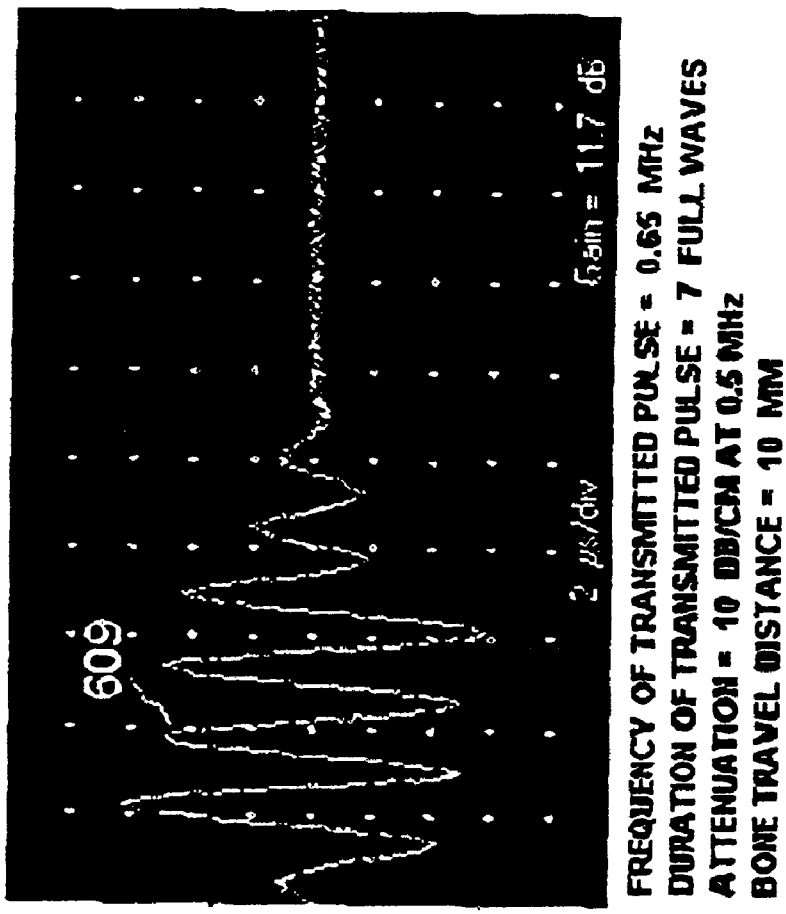
FIG.6 (CONTINUATION B)

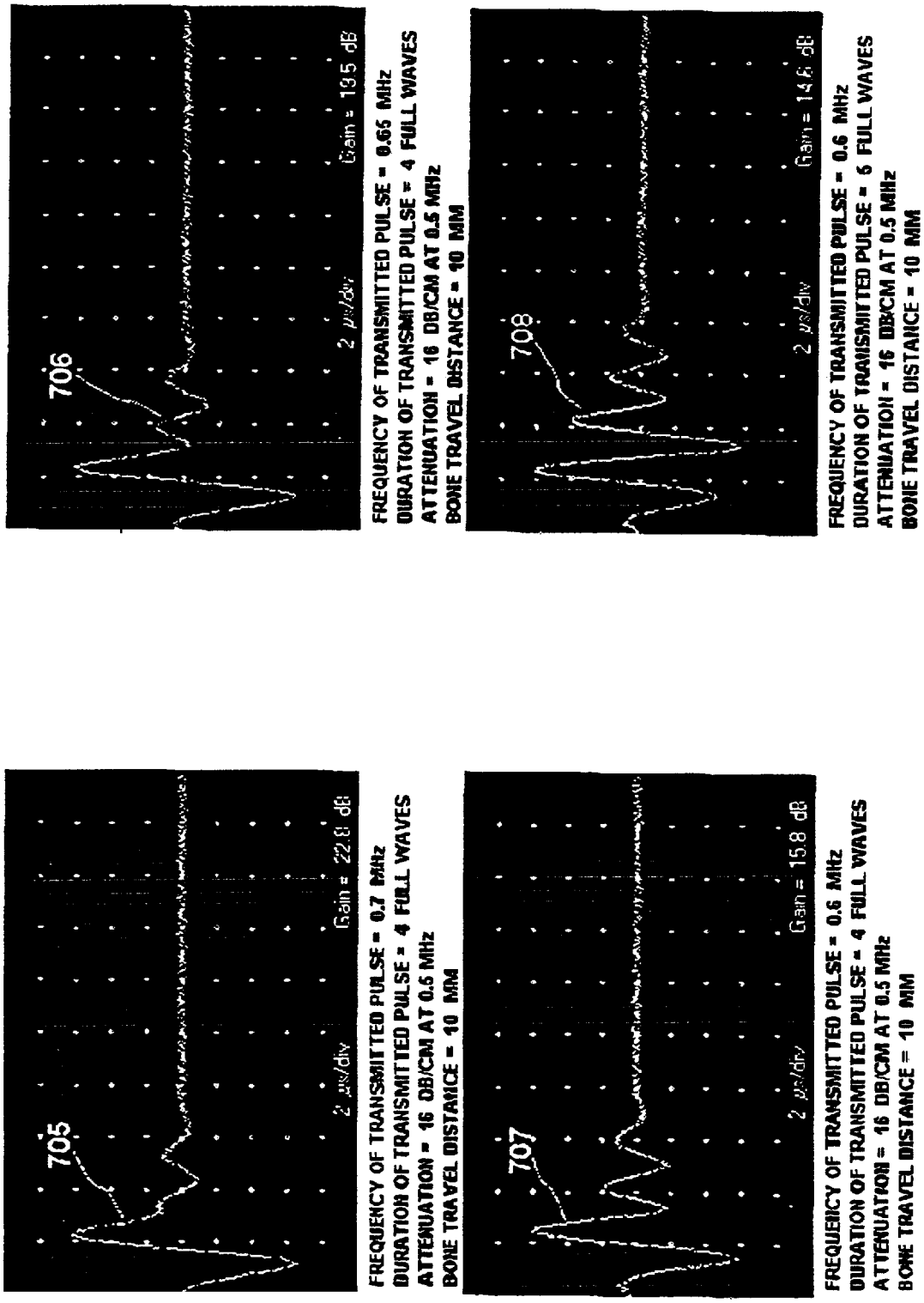
FIG.7 (CONTINUATION A)

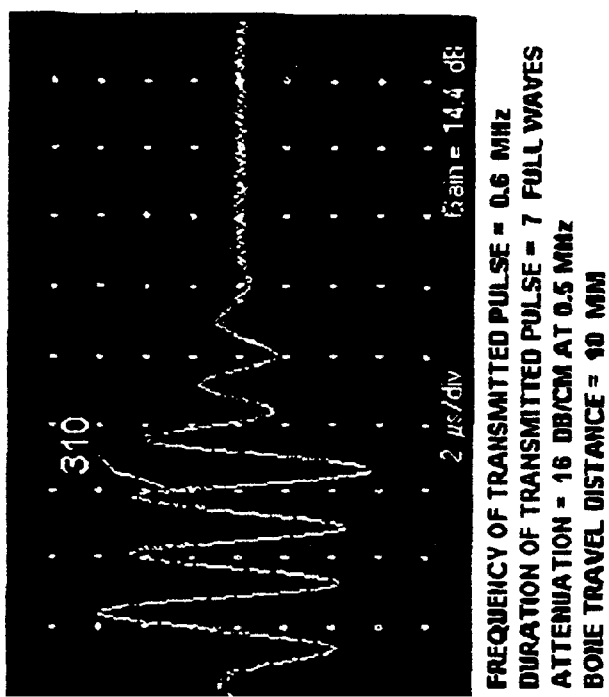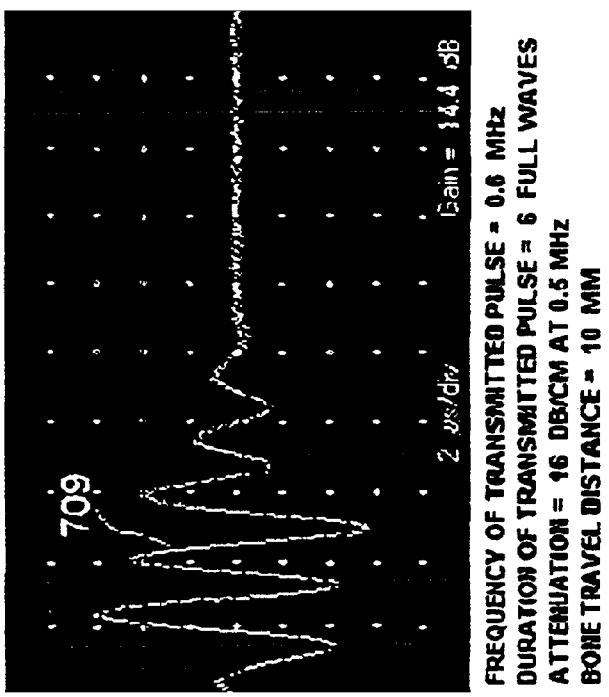
FIG.7 (CONTINUATION B)

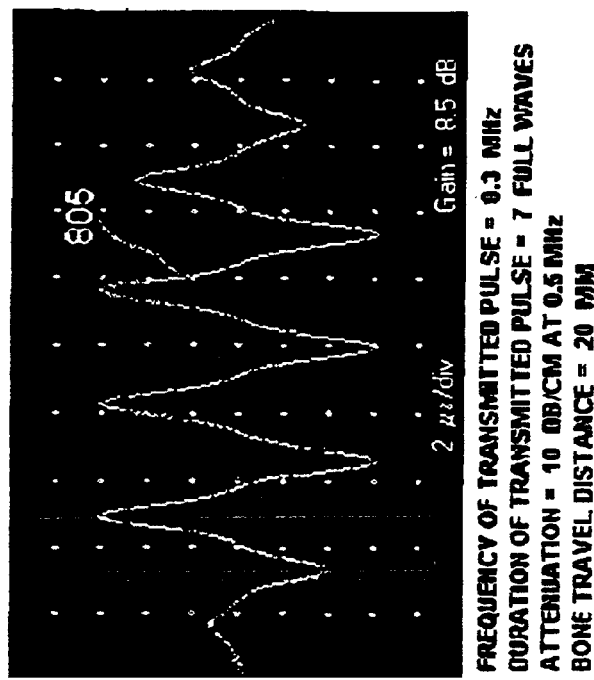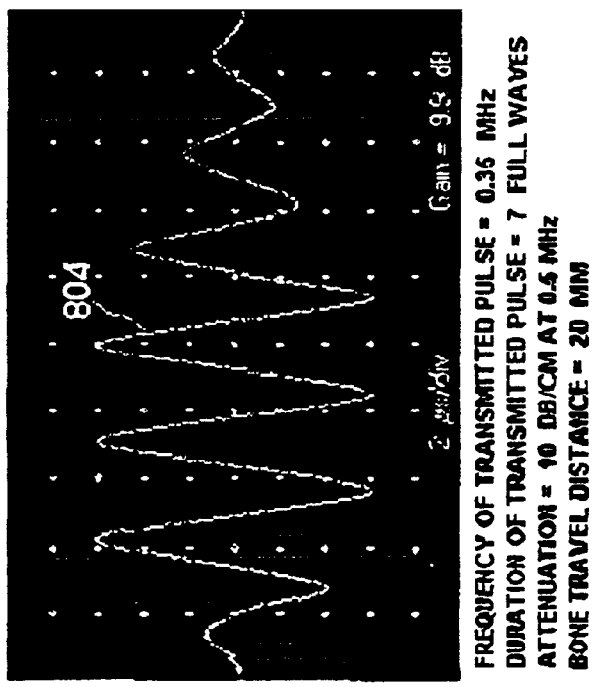
FIG.8 (CONTINUATION)

ULTRASONIC APPARATUS AND METHOD FOR EVALUATION OF BONE TISSUE

"This application claims priority from PCT/IL199/00563 filed Oct. 25, 1999, which claims priority from U.S. Provisional Application 60/105,568 filed Oct. 25, 1998."

FIELD AND BACKGROUND OF THE INVENTION

The present invention relates to ultrasonic tissue imaging techniques and, in particular, it concerns a method and apparatus for the ultrasonic evaluation of bone tissue.

It is known that ultrasonography is often used for diagnostic tissue imaging in human beings. As soft or fluid filled tissues possess favorable acoustic properties, ultrasonography is able to provide excellent imagine of these tissues. The ultrasonic evaluation of bone tissue, however (for example, for estimating the degree of osteoporosis, and thus bone fracture risk) is problematic, due to the difficulty in achieving adequate ultrasound penetration in complex solid biological structures Such as bone. To date, therefore, the reliable ultrasonic imaging of bone structure and density and has not been possible.

Ultrasonic evaluation of bone tissue, as with any biological tissue, is achieved by transmitting an ultrasonic pulse or pulses into the bone tissue, and then analyzing the acoustic qualities of the received reflected ultrasonic signals. Properties of bone tissue can then be determined by analyzing the amplitude and/or travel time of the received signals. The amplitude of the received pulses, which indicates the degree of attenuation of the transmitted ultrasound signals, correlates with bone mineral density. The travel time of the signal transmitted through the bone tissue is used for calculating the velocity of the ultrasound signal within the bone tissue, the so-called "speed of sound" (SOS), which also correlates with the degree of osteoporosis and/or risk of bone fracture.

Several techniques for the ultrasonic evaluation of bone tissue are known in the art. FIG. 1 depicts a conventional ultrasonic apparatus for evaluation of bone tissue, generally designated 10. Ultrasonic apparatus 10 for the evaluation of bone tissue includes an ultrasonic probe 12 for transmitting ultrasonic pulses towards a bone 14 via soft tissue 16, and for receiving signals reflected from or transmitted through, bone 14. Ultrasonic probe 12 is typically a hand-held implement for manipulation by an operator. The operator grips ultrasonic probe 12 and applies it to soft tissue 16. As the surface of bone 14 is inaccessible for direct coupling with ultrasonic probe 12, the operator is required to adjust the position and apposition of ultrasonic probe 12 on soft tissue 16, in order to optimize the transmission into, and reception from, bone 14 of ultrasound signals. When ultrasonic probe 12 is optimally oriented, the amplitude of the received signals is maximal while the time of flight is minimal.

Ultrasonic apparatus 10 for evaluation of bone tissue further includes a digital computing device 18 for analyzing the received ultrasound signal and generating an image of bone 14 from the measured amplitude and/or time delay of the received signal. Ultrasonic apparatus 10 for evaluation of bone tissue also includes a display 20 for displaying the image generated by computing device 18.

Turning now to FIG. 2, a part of ultrasonic apparatus 10 is depicted, including ultrasonic probe 12. As the internal structure of bone 14 is inhomogeneous, the ultrasound signal received by probe 12 typically has a low signal to noise ratio. As such, the through transmission technique is typically employed, in which one transducer (that is, a scanning crystal) transmits signals while a second transducer receives the signals after they have traveled through the substance under investigation.

Ultrasonic probe 12 typically includes two resonant scanning crystals 22 and 24, which work at a fixed frequency, and which are connected to digital computing device 18. Scanning crystal 22 is operative to transmit ultrasonic pulses toward bone 14 via soft tissue 16, while scanning crystal 24 is operative to receive ultrasonic signals which have passed through, or been reflected by, bone 14 and soft tissue 16. Each of scanning crystals 22 and 24 have inclined delay lines 26 and 28 respectively. In other words, the part of the transducer in front of the scanning crystal, through which the longitudinal waves generated by the scanning crystal pass prior to entering the tissue to which the transducer has been applied, is inclined at an acute angle to the surface of that tissue. The velocity of ultrasound within delay lines 26 and 28 is approximately equal to the velocity of ultrasound in soft tissue 16. Delay line 26 typically directs scanning crystal 22 at an angle $\alpha$ with regard to the surface of soft tissue 16, so as to cause propagation of longitudinal leaky waves along the surface of bone 14. Delay line 28 directs scanning crystal 24 by the same angle $\alpha$ with regard to the surface of soft tissue 16, so as to facilitate optimal reception of the ultrasound signal passed along bone 14.

The net travel time for ultrasound signals that have passed through bone 14 is described by the formula:

$$T_{14} = T_{\Sigma} - T_{26} - T_{28} - T_{16},$$

where $T_{14}$ is the net travel time for a signal passed through bone 14; $T_{\Sigma}$ is the time delay between transmission of an ultrasonic pulse by scanning crystal 22 and reception of the pulse by scanning crystal 24; $T_{26}$ and $T_{28}$ are the propagation times for ultrasonic pulses in delay lines 26 and 28 respectively; and $T_{16}$ is the propagation time for ultrasonic pulses in soft tissue 16.

Two auxiliary crystals 30 and 32 are located in ultrasonic probe 12, and are connected to digital computing device 18. Auxiliary crystals 30 and 32 are typically used to determine the propagation time for ultrasonic pulses in soft tissue 16. This is achieved by crystal 30 transmitting an ultrasonic pulse into soft tissue 16 while crystal 32 receives the reflected echo pulse from the surface of bone 14. The measured delay between transmission and reception of this echo pulse determines the value of $T_{16}$.

The velocity of ultrasound (SOS) in bone 14 is described by the formula:

$$SOS = \frac{BTD}{T_{14}}$$

Per the following reason:

It is well known that $$V[m/\text{sec}] = \frac{D\ [m]}{T\ [\text{sec}]}$$

SOS is defined as velocity; BTD is defined as distance and T is defined as time.

where BTD is the bone travel distance, which is determined by the distance between scanning crystals 22 and 24 and the value of angle $\alpha$.

Ultrasonic travel time and/or amplitude measurements for an ultrasonic pulse which has passed through bone 14 are heavily influenced by the proficiency with which the operator applies ultrasonic probe 12 to soft tissue 16. Several techniques for maximizing operator proficiency have been described in the art. A typical technique is illustrated in FIG. 3, in which a part of ultrasonic apparatus 10 is depicted, including ultrasonic probe 12. As shown in the figure, additional auxiliary crystals 34 and 36 are located within probe 12, and are connected to digital computing device 18. Crystal 34 is operative to transmit ultrasonic pulses into soft tissue 16, while crystal 36 is operative to receive the reflected echo pulse from the surface of bone 14. The measured delay between transmission and reception of said echo pulse is $T_{16a}$. When $I_{16}=T_{16a}$, probe 12 is oriented in such a way that the BTD will be the shortest possible for that probe. A smaller value for BTD minimizes the impact of inevitable inaccuracies in the calculation of SOS. Thus, when digital computing device 18 determines that $T_{16}=T_{16a}$, probe 12 is deemed to be oriented appropriately with regard to soft tissue 16, and the received echo signals are analyzed so as to image bone 14. When the condition $T_{16}\ T_{16a}$ is not met, received ultrasound signals are ignored by digital computing device 18.

In an alternative method for minimizing operator unreliability, the operator applies ultrasonic probe 12 to a reference block made from material with known acoustical properties prior to applying probe 12 to soft tissue 16 and bone 14. The operator can then compare the actual images obtained from bone 14 with the "optimal" images obtained from the reference block, and continues to adjust the orientation of probe 12 until such time as the current image approximates the "optimal images."

The above-described methods for ultrasonic imaging of bone, however suffer from several deficiencies:

1. It is common experience that the repeatability and precision of travel time and amplitude measurements for signals passed through bone 14 is low, even when optimal orientation of ultrasonic probe 12 with respect to bone 14 is achieved. Furthermore, as the exact propagation times $T_{26}$ and $T_{28}$ of ultrasonic signals in delay lines 26 and 28 are unknown, calculated values for ultrasound velocity (SOS) are unreliable.
2. The methods used for optimizing the orientation of probe 12 with regard to bone 14 do not relate to the signal actually received from bone 14, but rather, infer an optimal bone-probe orientation from signals received from other materials (either soft tissue 16 or a reference block).
3. As the dense cortex of bone 14 distorts transmitted signals, current fixed-frequency ultrasonic bone imaging techniques allow only for an integral evaluation of the surface of bone 14, but not for the imaging of the internal structure of bone 14 (for example, so as to reveal local inhomogeneities and fractures). Furthermore, as current techniques utilize ultrasonic pulses of a single, fixed, frequency- and measure only amplitude or travel time changes in the received signal-additional ultrasonic phenomena, such as possible changes in the frequency spectrum of the transmitted pulse induced by the internal structure of bone, are not evaluated. Such phenomena, however, may reveal information about the internal structure of bone, which cannot be inferred from single parameter measurements (such as amplitude or travel time).

There is therefore a need for, and it would be highly advantageous to have a method and device for achieving ultrasonic imaging of bone tissue which would allots for the precise and easily repeatable measurement of ultrasonic travel time and signal amplitude, the imaging of the internal structure of bone tissue, and the optimization of probe orientation by directly utilizing the imaging signals received from the bone.

SUMMARY OF THE INVENTION

The invention is a method and device for the ultrasonic imaging of bone tissue.

According to the teachings of the present invention there is provided, a method for ultrasonic imaging of bone tissue, including the steps of transmitting a repeating ultrasonic signal into the bone tissue, the ultrasonic signal having a frequency and containing a number of full waves; receiving the transmitted signal; determining the number of full waves in the received signal; defining, as a first definition, whether or not the determined number of full waves in the received signal is equal to the number of full waves in the transmitted repeating ultrasonic signal; and modifying the frequency of the transmitted repeating ultrasonic signal in accordance with the first definition. There is further provided a method for optimizing the orientation of an ultrasound probe on bone tissue, including the steps of transmitting an ultrasound signal into the bone tissue from a transmitter in the ultrasound probe; receiving the transmitted ultrasound signal by a first receiver in the ultrasound probe; receiving the transmitted ultrasound signal by a second receiver in the ultrasound probe, the second receiver being displaced from the first receiver, in relationship to the transmitter; and correlating the ultrasound signal received by the first receiver with the ultrasound signal received by the second receiver. There is further provided a bone tissue ultrasonic imaging system, including a first wide band scanning crystal for transmitting an ultrasonic signal into the bone tissue; a frequency selection mechanism for selecting a frequency for the transmitted ultrasonic signal; a full wave quantity selection mechanism for selecting a quantity of full waves for the transmitted ultrasonic signal; a second wide band scanning crystal for receiving the transmitted ultrasonic signal; a full wave quantity counting mechanism for counting a quantity of full waves in the received ultrasonic signal, and inputting to the frequency selection mechanism a desired output frequency; a waveform analyzing mechanism for analyzing waveforms in the received ultrasonic signal, inputting to the frequency selection mechanism a desired output frequency, and inputting to the full wave quantity selection mechanism a desired quantity of full waves for the transmitted ultrasonic signal. There is further provided a system for optimizing the orientation of a bone ultrasonic imaging probe, including a first wide band scanning crystal for transmitting an ultrasonic signal into the bone tissue; a second wide band scanning crystal for receiving the transmitted ultrasonic signal; a third wide band scanning crystal for receiving the transmitted ultrasonic signal, the third wide band scanning crystal being displaced from the second wide band scanning crystal, in relationship to the first wide band scanning crystal; and a mechanism for correlating the received ultrasonic signal from the second wide band scanning crystal with the received ultrasonic signal from the third wide band scanning crystal.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is a method and device for achieving ultrasonic imaging by bone tissue. By "imaging" is meant the acquisition or derivation of any ultrasonic. variable or function that correlates with the internal structure of a bone tissue under ultrasonic interrogation. Once the variables or functions have been acquired they may then be used to create a display depicting the anatomy and structure of the tissue. The current invention relates primarily to novel techniques for acquiring and deriving reliable ultrasonic imaging data from bone tissue. A variety of existing techniques for displaying such imaging data may then be used to generate a graphic depiction of the bone under investigation.

The crystal principles and operation of a method and device for achieving ultrasonic imaging of bone tissue, according to the present invention, may be better understood with reference to the drawings and the accompanying description.

Figure 1:
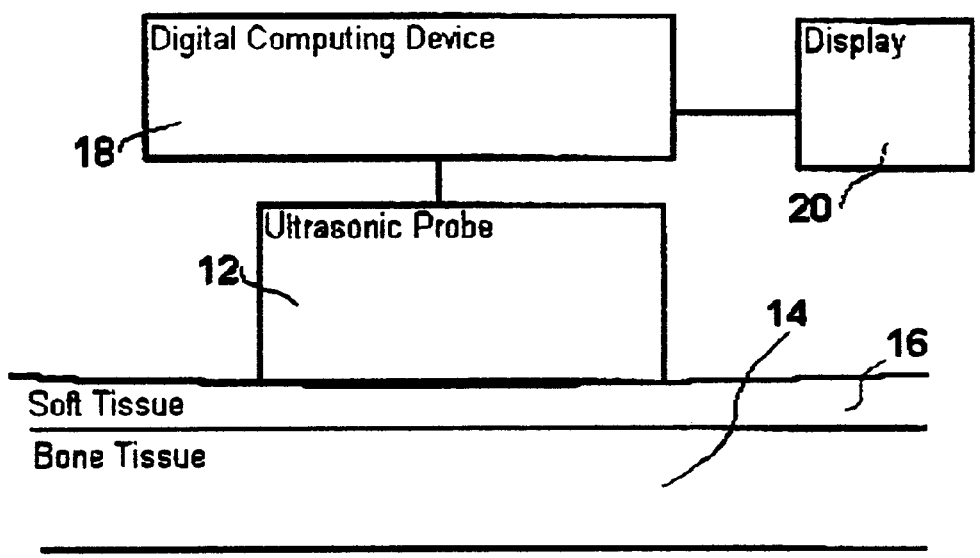
FIG. 1 is a schematic illustration of a conventional ultrasonic apparatus for imaging bone tissue.
Figure 2:
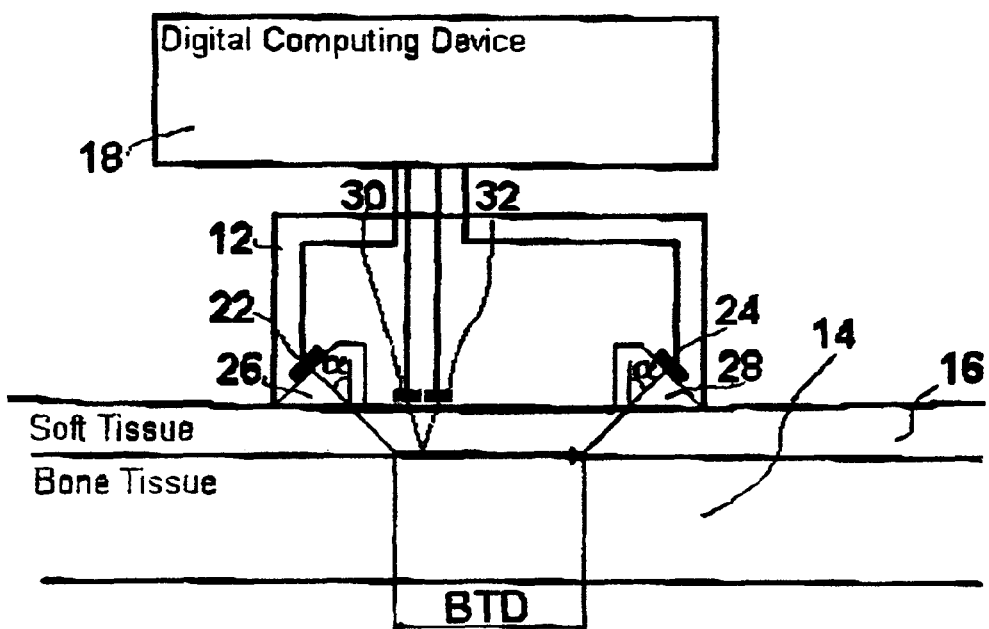
FIG. 2 is a schematic illustration, in cross section, of a conventional ultrasonic apparatus for imaging bone tissue.
Figure 3:
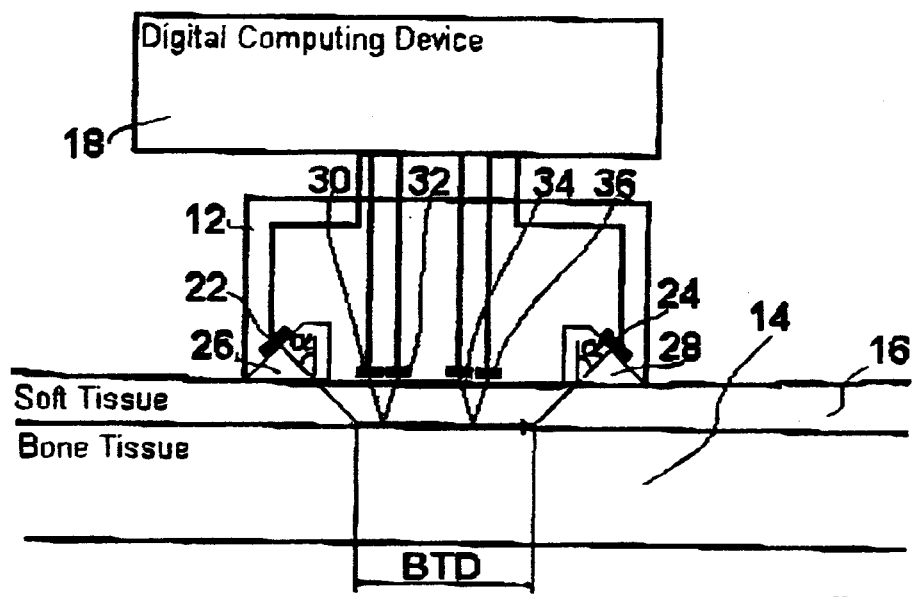
FIG. 3 is a schematic illustration, in cross section, of a conventional ultrasonic apparatus for imaging bone tissue, including an ultrasonic probe with two scanning ultrasonic crystals and two auxiliary ultrasonic crystals.
Figure 4:
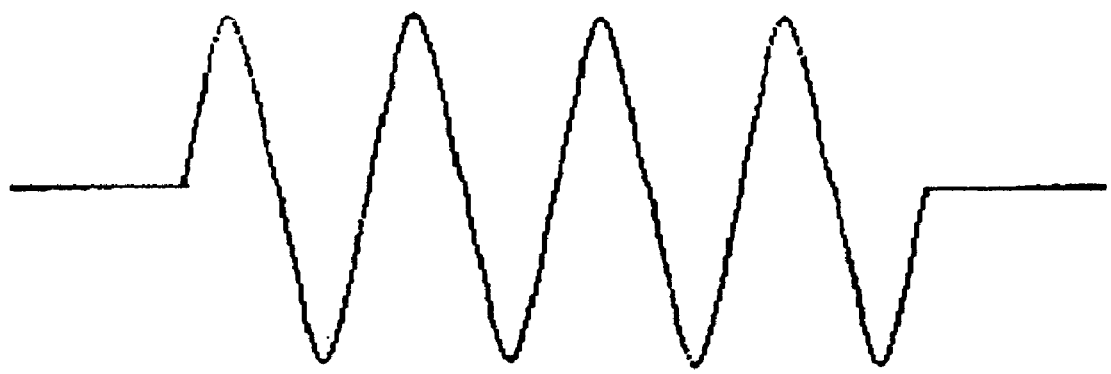
FIG. 4 is a diagram of the waveform of an experimentally transmitted ultrasound pulse.
Figure 5:
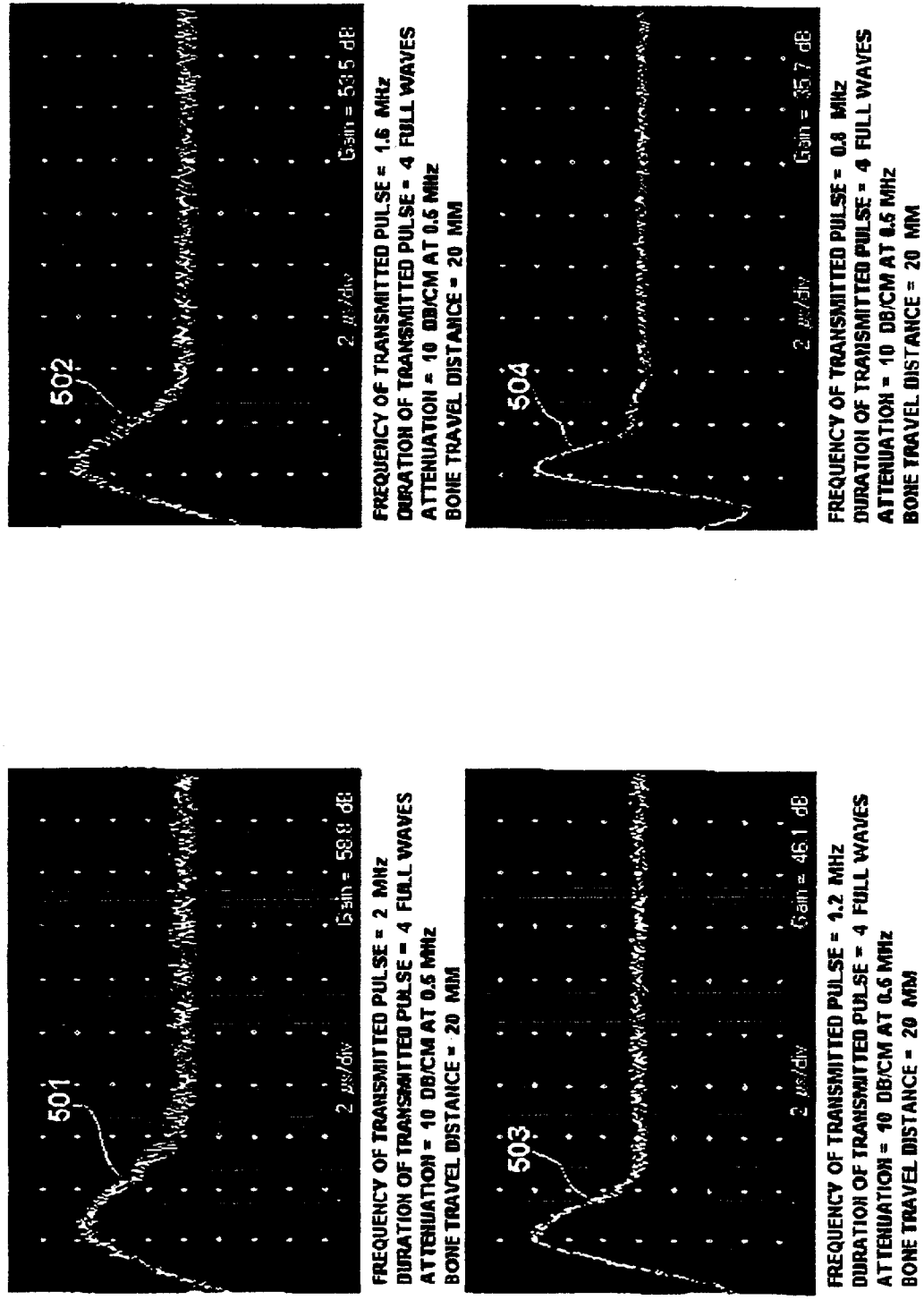
FIG. 5 is a first example of scope screenshots of experimental signals passed through bone tissue.

Tuning now to FIGS. 4 and 5, the results of experimental transmission of ultrasonic signals into bone tissue by a wide band ultrasonic crystal are shown. The waveform of the transmitted ultrasonic signal is depicted in FIG. 4. In FIG. 5 the oscilloscope screenshots show the ultrasonic signal received by a second wide band ultrasonic crystal after transmission, into bone tissue, of a single ultrasonic pulse comprising four waves. In all the examples demonstrated in FIG. 5, the bone travel distance for the ultrasonic pulse was 20 mm and the attenuation of the ultrasonic wave on the surface of the bone tissue as 10 dB/cm at 0.5 MHz. In signals 501 through 508, the frequency of the transmitted pulse was progressively decreased, from 2 MHz to 0.55 MHz. It is noteworthy that in signals 501 through 504, in which the transmission frequency was high, the received signal comprised only a single wave, whereas in signals 505 through 508, as the transmission frequency decreased towards 0.55 MHz, additional wave components became discernable. At a transmission frequency of 0.55 MHz, four wave components were consistently discernable, indicating that the received signal was of a similar wave composition to that of the transmitted pulse. These results demonstrate that when ultrasound pulses are transmitted into bone tissue at excessively high frequencies, the received signal is highly deformed with respect to the transmitted pulse. When the transmission frequency is appropriate (in the demonstrated example: 0.55 MHz), however, the waveform of the transmitted pulse is preserved.

As can be seen in FIG. 5, the four waves constituting the received pulse in signal 508 were each of different amplitude. In signals 509 through 511 the transmission frequency was kept constant, while the number of waves in the transmitted pulse was gradually increased. Signal 511 demonstrates that a steady state was achieved (wherein at least 2 consecutively received waves were of identical amplitude) when the transmitted pulse comprised seven waves. The transmitted signal comprised an integer number of half waves of a sinusoid.

Figure 6:
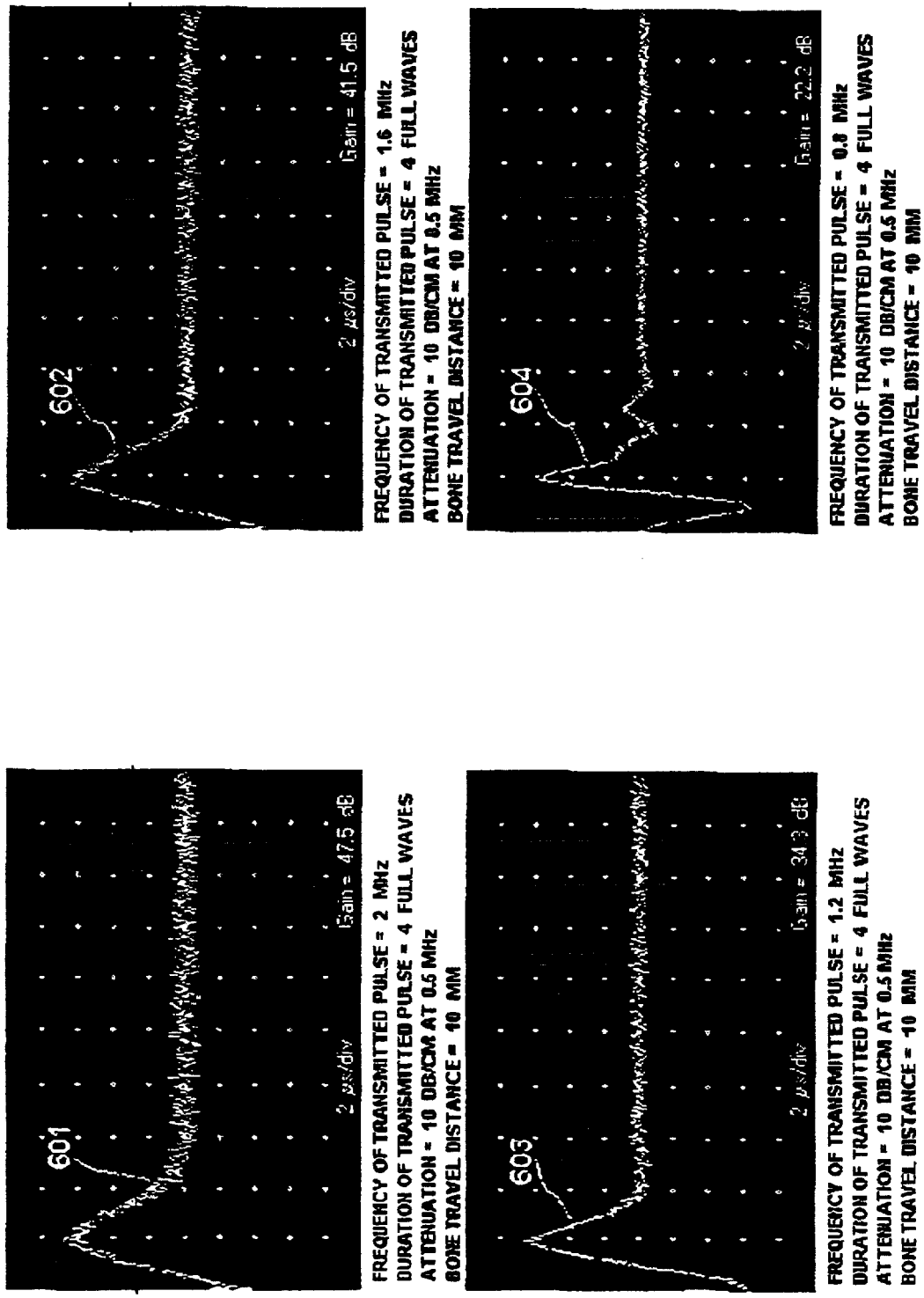
FIG. 6 is a second example of scope screenshots of experimental signals passed through bone tissue.

FIG. 6 shows the results of a similar experiment to that described in FIG. 5, except that the bone travel distance was shorter (10 mm rather than 20 mm). The results of this experiment were consistent with those of the experiment shown in FIG. 5. In this experiment, the transmission frequency at which the waveform of the transmitted pulse was preserved was found to be 0.65 MHz. As in FIG. 5, increasing the number of waves in the transmitted pulse to seven resulted in a steady state for amplitude of the received waves being achieved.

Figure 7:
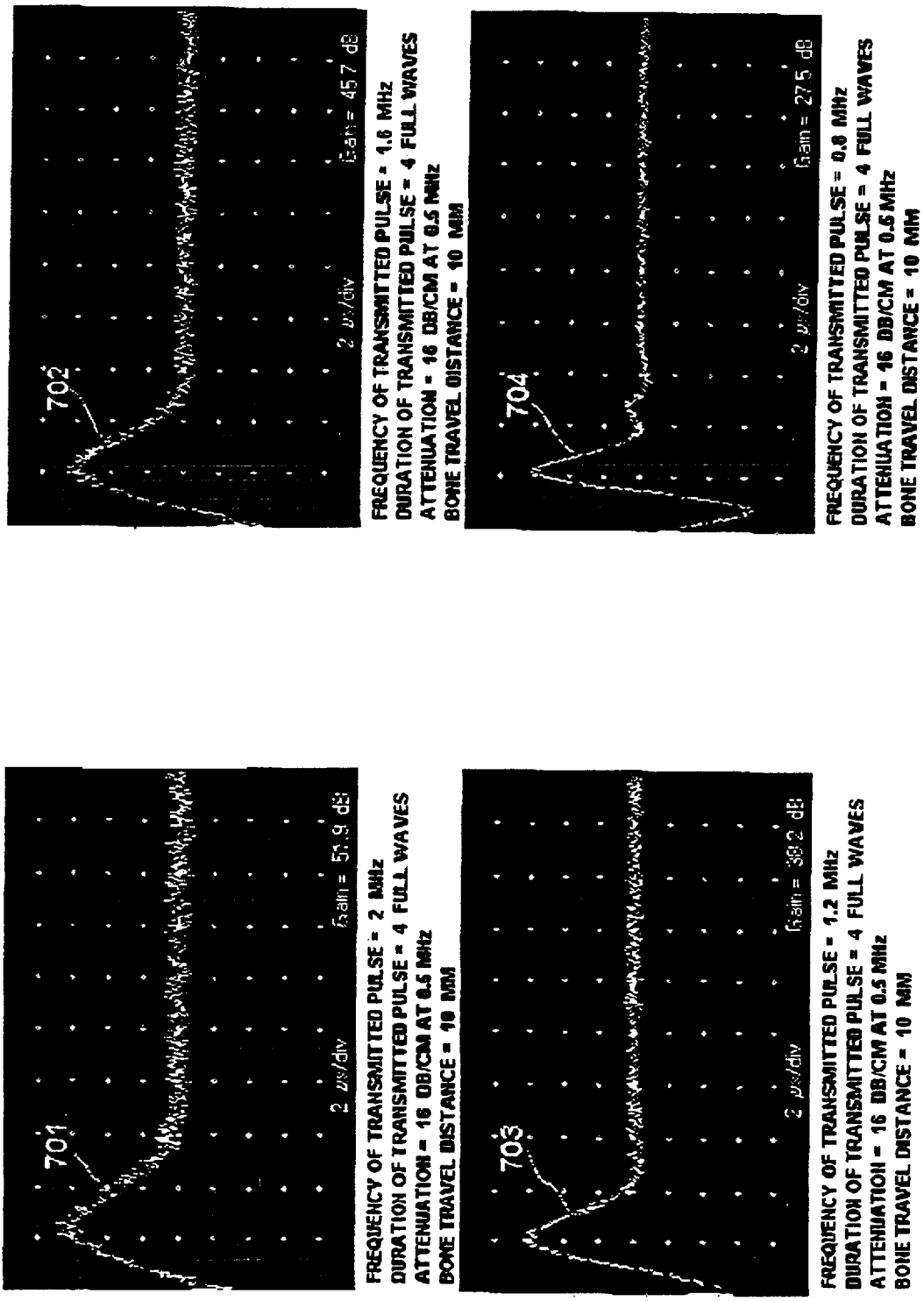
FIG. 7 is a third example of scope screenshots of experimental signals passed through bone tissue.

FIG. 7 shows the results of a similar experiment to that described in FIG. 6, except that the attenuation of the transmitted pulse was greater than that of the transmitted pulse in FIG. 6(16 dB/cm as opposed to 10 dB/cm, at 0.5 MHz). The results of this experiment were consistent with those of the experiments shown in FIGS. 5 and 6. In this experiment, the transmission frequency at which the waveform of the transmitted pulse was preserved was found to be 0.6 MHz. As in FIGS. 5 and 6, increasing the number of waves in the transmitted pulse to seven resulted in a steady state for amplitude of the received waves being achieved.

These experiments show that when transmitting ultrasound signals into bone tissue, the quantity of full waves in the received signal approaches, and eventually becomes equal to, the quantity of full waves in the transmitted pulse, as the frequency of the transmitted pulse is progressively reduced. It should be emphasized that, as will be well known to one familiar with acoustic theory, reception of an ultrasonic pulse having an equal number of full waves to that of the transmitted pulse indicates that the transmitted pulse successfully penetrated at least pail of the bone tissue under interrogation.

This phenomenon is of crucial relevance to ultrasonic bone imaging techniques because the accurate calculation of time of flight and amplitude attenuation of received ultrasound waves is feasible only when the received signal is comparable to the transmitted signal in terms of its waveform, that is, when penetration of the transmitted signal has occurred. Distortion of the transmitted wave during propagation through tissue (due to incomplete penetration) prohibits meaningful comparison of the amplitudes and times of flight of the transmitted and received waves. As described above, standard ultrasonic imaging techniques utilize fixed, single frequency, transducers, the frequency of which bear no relevance to local bone conditions and are usually inappropriate for that bone. Furthermore, standard ultrasonic imaging techniques provide no mechanism for indicating to the user whether or not penetration of the bone tissue by the transmitted wave has actually been achieved.

The phenomenon of frequency-induced wave distortion in bone tissue thus renders standard ultrasonic imaging techniques inadequate for use on bone tissue, usually precluding imaging of the internal structure of bone as well as precluding precise measurement of amplitude and travel time.

The critical frequency at which the equalization of transmitted and received waveforms occurs is thus the upper limit for the frequency at which ultrasonic interrogation of bone tissue can be meaningfully performed. The experiments reported in FIG. 5, FIG. 6 and FIG. 7 show that the value of this upper frequency limit depends on the properties of the particular bone tissue under interrogation (for example, ultrasonic attenuation in the bone) and on the bone travel distance (i.e. the distance between the scanning crystals in the ultrasonic probe).

The experimental results reported above also demonstrate that for meaningful ultrasonic imaging of bone tissue to be performed, it is necessary to optimize the frequency of the transmitted ultrasound pulse in accordance with local bone tissue conditions.

As can be seen in signals 511, 609, and 710, in which optimal transmission frequencies have been achieved, a signal optimally propagated through bone tissue comprises two parts: a transient process part (during which the amplitude and waveform of the signal are in flux) and a stationary part (during which a steady state waveform corresponding to the transmitted waveform is achieved). The phenomenon of frequency-induced wave distortion in bone tissue (as demonstrated above in the experiments of FIGS. 5, 6, and 7) occurs due to a long transient process that occurs in solid, complex tissues. At a critical frequency, however, the duration of the transient process in the bone tissue becomes shorter than the pulse duration of the signal transmitted into the bone under interrogation. When this occurs, the bone becomes saturated by a transmitted wave of such a nature that the reflected wave will be identical in shape, and thus suitable for imaging analysis. (When the duration of the transient process in the bone tissue is longer than the pulse duration of the transmitted signal, however, the bone will be saturated in a manner that does not allow for meaningful analysis of the reflected wave.) It is at this critical frequency that the equalization of transmitted and received waveforms demonstrated in the experiments of FIGS. 5, 6, and 7 occurs.

The stationary part of the propagated signal is of importance inasmuch as it is the only component of the signal suitable for analysis so as to calculate signal time of flight and/or changes in amplitude precisely. High precision measurement of time of flight and/or amplitude can be performed by comparing the amplitude (positive, negative or peak-to-peak) of the first full wave in the stationary part of the received signal with the corresponding wave in the transmitted pulse. As is well known in the art, when measuring distances by means of time of flight calculations, it is desirable that the signal be as short as possible. When interrogating bone tissue with ultrasound it is thus desirable to utilize a transmitted signal which is as short as possible, yet long enough to establish a measurable stationary part.

Figure 8:
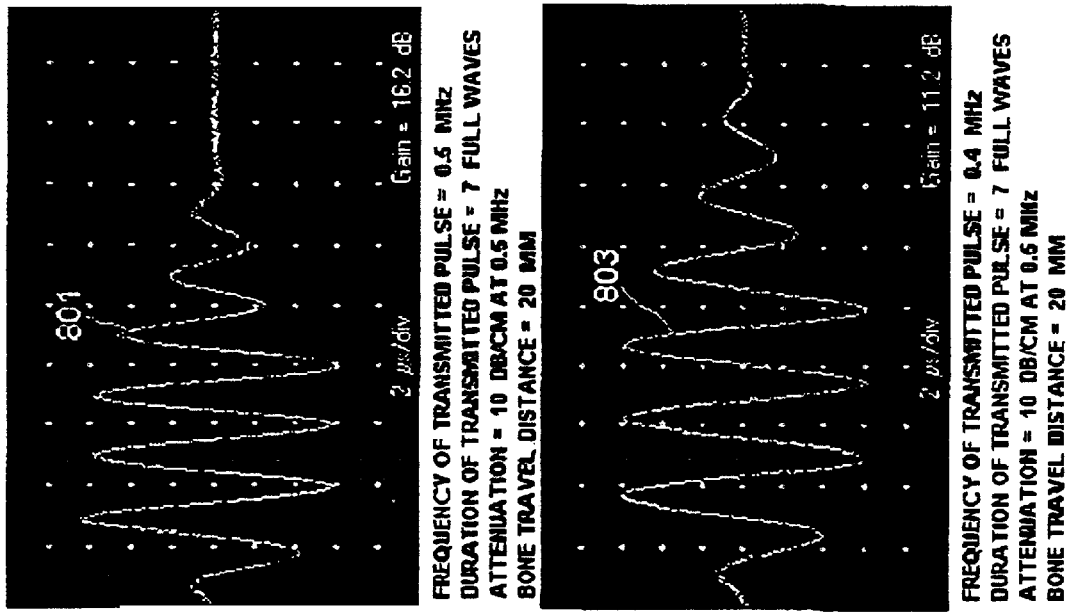
FIG. 8 is a fourth example of scope screenshots of experimental signals passed through bone tissue.
Figure 8:
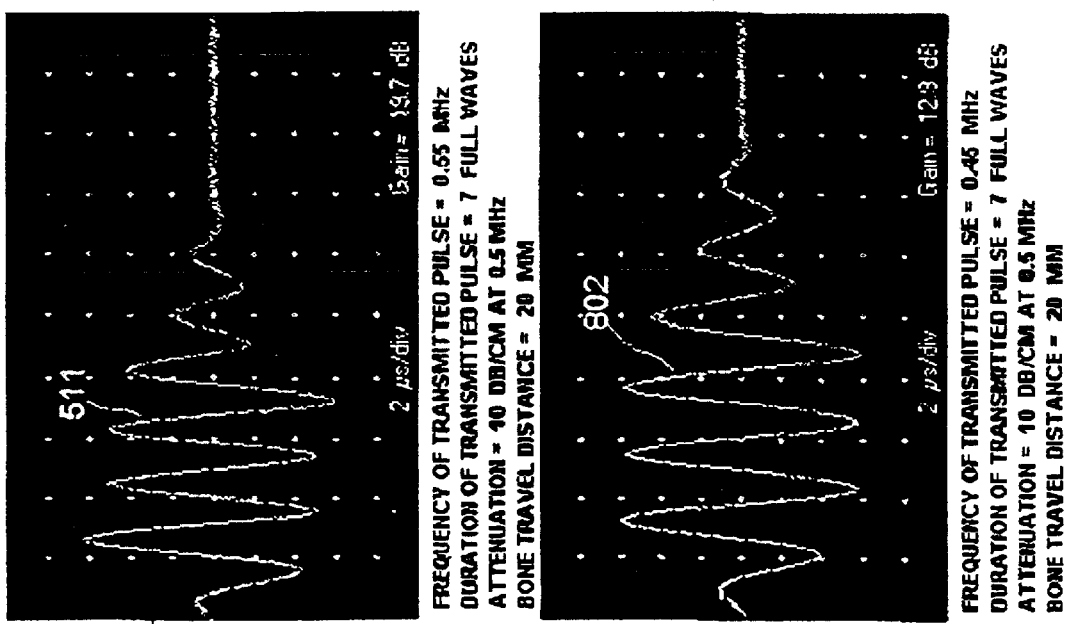

Turning now to FIG. 8, additional results of experimental transmission of ultrasonic signals, by a wide band ultrasonic crystal, into the same bone tissue as used in the experiments of FIGS. 5, 6, and 7 are shown. The oscilloscope screenshots show the ultrasonic signal received by a second wide band ultrasonic crystal after transmission, into the bone tissue of a single ultrasonic pulse comprising seven waves. In all the demonstrated examples, the bone travel distance for the ultrasonic pulse was 20 mm and the attenuation of the ultrasonic wave on the surface of the bone tissue was 10 dB/cm at 0.5 MHz. The frequency of the first transmitted pulse (signal 511) was 0.55 MHz, and in each subsequent pulse (signals 801 through 805) the transmission frequency was decremented by 0.05 MHz at a time, as indicated in the figure. Thus, the first ultrasonic pulse transmitted, which resulted in reception of signal 511, had a frequency corresponding to the upper limit for meaningful interrogation of the local bone tissue, while the quantity of transmitted full waves was sufficient to result in an easily detectable stationary part in received signal 511, as described above. It is noteworthy that as the frequency of the transmitted ultrasonic pulse was decreased, the stationary part of the received signal became progressively more elongated (see signals 801 through 804). Signal 805 demonstrates that at a critical frequency (in this case 0.3 MHz) the waveform of the received signal became deformed in the zero cross area (that is, the point on the time axis where the signal is equal to zero, when passing from a positive value to a negative value, or vice-versa). When the multilayered bone tissue becomes fully saturated by the transmitted wave, the interferential wave (i.e. a complex wave consisting of multiple wave modes, similar to a Lamb wave, which is propagated through the tissue) becomes non-linear due to harmonics caused by oscillation of all the bone layers. This phenomenon, which is well described in non-linear acoustic theory, results in the deformatioll of the received wave, as observed in signal 805. As deformation of this nature precludes meaningful analysis of the received signal and comparison with the transmitted signal, this critical frequency constitutes the lower limit for the frequency at which ultrasonic interrogation of this bone tissue can be meaningfully performed. Below this frequency, distortion of the pulse waveform renders calculation of amplitude and time delay unreliable. The value of this lower frequency limit depends on the properties of the particular bone tissue under interrogation (for example, ultrasonic attenuation in the bone) and on the bone travel distance (i.e. the distance between the scanning, crystals in the ultrasonic probe). It should also be noted in FIG. 8 that as the transmission frequency was decreased from 0.55 MHz to 0.35 MHz, the net travel times for signals 801 through 804 increased (as indicated by an elongation of the stationary part of the signal) and the amplitudes of the signals increased, even though the bone travel distance remained constant. This phenomenon, of ultrasound velocity and amplitude in bone tissue being dependent on the ultrasound transmission frequency, is a manifestation of two ultrasonic phenomena:

1. Due to the multiple tissue layers from which bone is structured, the mode of a propagated ultrasonic wave changes from being purely longitudinal to being a complex of different modes (referred to above as an interferential wave, similar to a Lamb wave) as it passes through bone tissue. As the nature of this wave-complex is dependent on the frequency of the transmitted wave, two transmitted waves of different frequency passing through the same bone, will have different travel times 2. Ultrasound waves of different frequencies possess different penetration capabilities, and thus different travel times.

It will be well known to one familiar with linear and non-linear acoustic theory that an ultrasonic pulse transmitted into bone will be propagated within the bone tissue as a spectrum of frequencies, with the width of the spectrum being dependent on the shape of the pulse. A transmitted pulse can therefore be resolved into a number of sinusoids, each sinusoid having its own amplitude and frequency. Due to the above-described phenomenon of frequency dependent attenuation of the ultrasonic signal, the output signal will differ from the input signal in terms of its constituent sinusoid amplitudes and frequencies. These amplitudes and frequencies can be analyzed so as to derive information about the internal structure of the bone under investigation.

Figure 9:
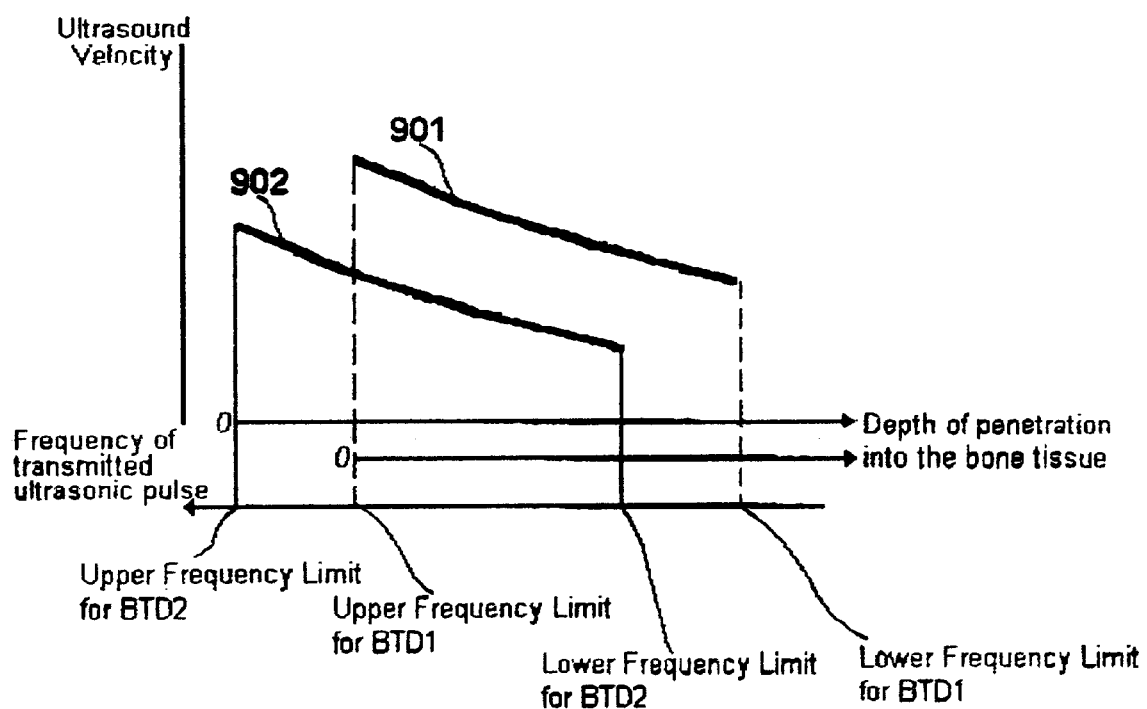
FIG. 9 is a graph depicting ultrasound velocity as a function of depth of penetration into bone tissue.

Turning now to FIG. 9, an example of ultrasound velocity presented as a function of depth of penetration into bone tissue is shown. Two curves are shown in FIG. 9 Curve 901 corresponds to a first bone travel distance BTD1, being the distance between the transmitting and receiving crystals of a first ultrasonic probe, and curve 902 corresponds to a second bone travel distance BTD2, being the distance between the transmitting and receiving crystals of a second ultrasonic probe. Curves 901 and 902 both depict the results of ultrasonic transmission through the same bone tissue, with BTD1 being greater than BTD2. As shown, for a given BTD, changing the frequency of the transmitted pulse results in a different net travel time (i.e. a different ultrasound velocity) for the ultrasound signal. The upper and lower frequency limits for meaningful ultrasonic interrogation of the bone tissue, as described in the experiments of FIGS. 5, 6, 7, and 8, are marked on the X axis of the graph. Initial penetration of the bone tissue commences when the transmission frequency is equal to the upper frequency limit (marked by a zero on the graph). At frequencies higher than this, incomplete penetration of the bone tissue by the transmitted pulse results in distortion of the received signal. Starting from the upper frequency limit, as the transmission frequency decreases the depth of penetration progressively increases, until such time as the lower frequency limit is achieved. At this point the bone tissue is fully saturated, and further decreasing the transmission frequency results in distortion of the received signal. As thicker bone tissue will become fully saturated at a lower transmission frequency than will thinner bone tissue, the thickness of a layer of bone tissue correlates with the difference between the observed upper and lower limits for appropriate transmission frequencies for a fixed bone travel distance (i.e. for an ultrasonic probe with a fixed distance between the scanning crystals). Furthermore, for a given transmission frequency, increased bone mineral density is associated with a decrease in the velocity of ultrasound within the bone tissue. Thus both thickness of the bone under investigation and its mineral density can be imaged in terns of the relationship between transmission frequency and measured ultrasound velocity.

The reliability and quality of ultrasonic bone imaging can therefore be markedly improved by performing multifrequency measurements of travel times and/or amplitudes of signals passed through the bone tissue, alter adapting the frequency and duration of the transmitted pulse so as to achieve an optimal received signal (that is, a received signal of identical number of waves to that of the transmitted signal).

The innovation of the current invention lies in achieving ultrasonic bone imaging by utilizing any or all of the following techniques (which have been demonstrated in the above experiments):

1. optimizing the transmitted signal frequency to an upper frequency limit such that the received signal is of an identical number of waves to that of the transmitted signal (so as to ensure that amplitude and time-of-flight calculations are meaningful)
2. optimizing the number of waves in the transmitted signal such that the received signal includes two consecutive waves of identical amplitude (so as to ensure that amplitude and time-of-flight calculations are meaningful)
3. determining a lower frequency limit for the transmitted signal such that the received signal begins to show distortion in the zero cross area (so as to image the thickness of bone tissue as a function of the difference between the upper and lower transmission frequency limits, and image the bone mineral density by measuring ultrasound velocity as a function of depth of penetration of the transmitted signal)
4. determining the amplitude and frequency spectrum of sinusoids of a received wave (so as to image bone characteristics as a function of sinusoidal frequency spectra).

Figure 10:
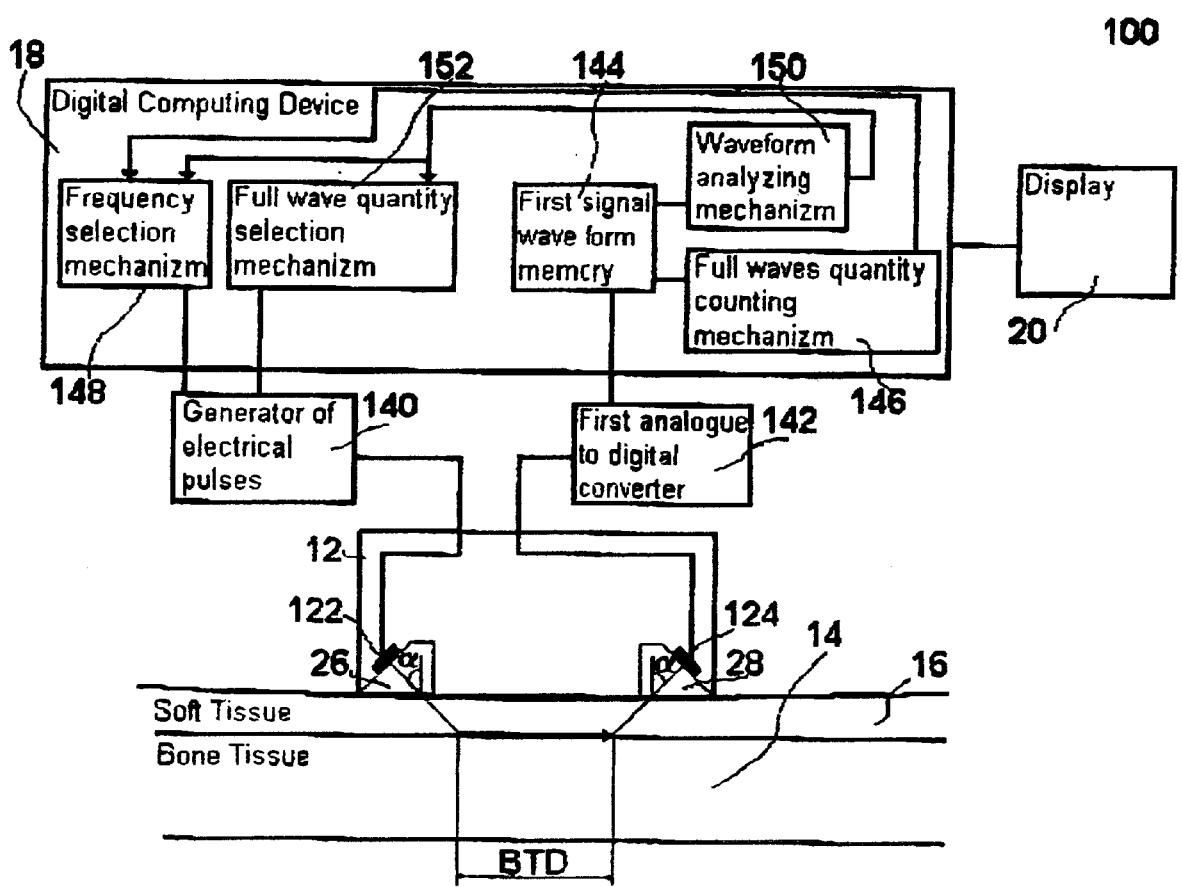
FIG. 10 is a schematic illustration of a first preferred embodiment of an ultrasonic apparatus for imaging bone tissue.

Referring now to the drawings, FIG. 10 is a block diagram of a first preferred embodiment of an ultrasonic apparatus for imaging bone tissue, generally designated 100, constructed and operative according to the teachings of present invention. Ultrasonic apparatus 100 is similar to ultrasonic apparatus 10 and therefore common elements are denoted with similar reference numbers used to describe ultrasonic apparatus 10.

Hence, ultrasonic apparatus 100 includes ultrasonic probe 12 for transmitting ultrasonic pulses into bone 14 via soft tissue 16, and for receiving reflected or transmitted signals therefrom. Ultrasonic apparatus 100 further includes digital computing device 18 for analyzing the received ultrasound signal and generating an image of bone 14 from the measured amplitude and/or time delay of the received signal. Ultrasonic apparatus 100 also includes display 20 for displaying the image generated by computing device 18.

Figure 11:
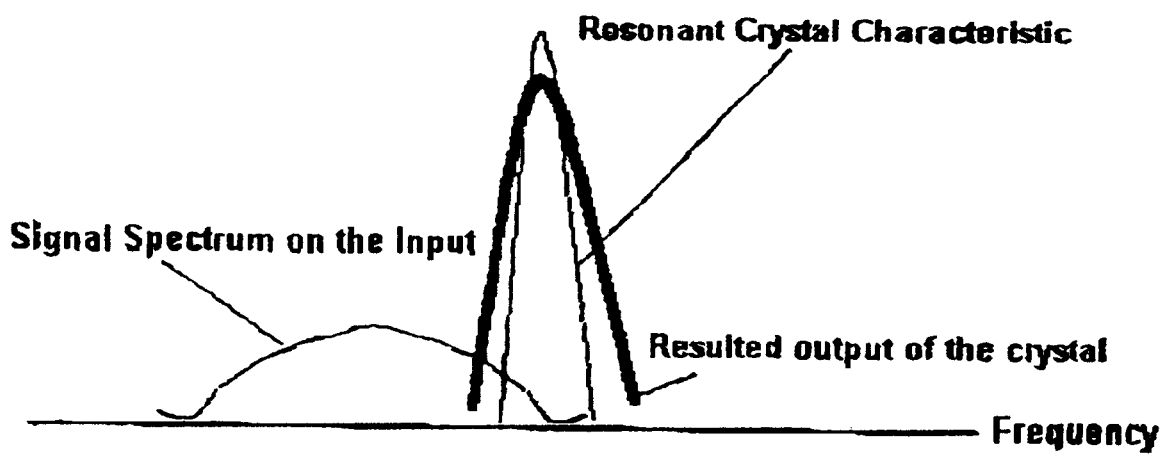
FIG. 11 is a diagram of ultrasound frequencies received and transmitted by a resonant crystal.

It is a particular feature of apparatus 100 that ultrasonic probe 12 includes two wide band scanning crystals 122 and 124. It should be noted that wide band scanning crystals differ significantly from resonant scanning crystals (which are used in the prior art), inasmuch as resonant scanning crystals exhibit the characteristic of frequency dependent transfer function. Consequently, when a resonant scanning crystal converts an acoustic signal into an electrical signal (or vice-versa), the resonance of the crystal itself interferes with the resonance of the received (or transmitted) signal. FIG. 11 illustrates the nature of this interference. As shown in the figure, the frequency of the signal output by a resonant scanning crystal is a summation of the frequency spectra of the received signal and the frequency spectra of the crystal itself. Thus, when standard resonant crystals are used to receive signals propagated through bone tissue, the response of the receiving crystal, rather than the response of the bone tissue alone, is measured, resulting in imprecise calculation of signal travel time and/or changes in amplitude. Wide band scanning crystals, however, convert acoustic signals into electrical signals (or vice-versa) with high fidelity, preserving the full frequency spectra of the received signal. An additional difference between wide band and resonant scanning crystals is that whereas resonant crystals oscillate at a fixed frequency, the transmission frequency of wide band crystals can be varied.

Standard wide band scanning crystals of the type well described in the literature (Brown A. F. and Weight I. P. "Generation and reception of wide-band ultrasound", published in Ultrasonics, 1974, v.12, No4, p.161–167, and Mitchell B. F. and Redwood M. "The generation of sound by nonuniform piezoelectric materials", published in Ultrasonics, 1969, v.7, No7, p.123–129) are suitable for use as wide band scanning crystals 122 and 124. Wide band scanning crystal 122 is operative to transmit ultrasonic pulses into bone 14 via soft tissue 16, while wide band scanning crystal 124 is operative to receive the transmitted and reflected ultrasonic signals after having passed through bone 14 and soft tissue 16. In terms of the teaching of the current invention, wide band scanning crystals 122 and 124 allow for tuning of the frequency of transmitted ultrasonic pulses, so as to optimize the frequency of transmitted ultrasound pulses according to local bone tissue conditions.

Returning now to FIG. 10, inclined delay lines 26 and 28 equip scanning crystals 122 and 124 correspondingly. The values of ultrasound velocities for delay lines 26 and 28 are approximately equal to the value of ultrasound velocity in the soft tissue 16. Delay line 26 directs scanning crystal 122 by the angle α providing propagation of ultrasonic wave along the surface of bone 14. Delay line 28 directs the scanning crystal 124 by the same angle α providing optimal receiving of signal passed along the bone 14.

The net travel time for signal passed through bone 14 is determined by the following way:

$$T_4 = T_\Sigma - T_{26} - T_{28} - T_{16},$$

here $T_{14}$ is the net travel time for signal passed through bone 14;

$T_\Sigma$ is the delay of signal received by scanning crystal 24 with respect to ultrasonic pulse transmitted by scanning crystal 22;

$T_{26}$ and $T_{28}$ are the propagation times of ultrasonic pulse in the delay lines 26 and 28 correspondingly;

$T_{16}$ is the propagation time of ultrasonic pulse in the soft tissue 16.

The ultrasound velocity (SOS) in the bone 14 is determined by digital computing device by the following way:

$$SOS = \frac{BTD}{T_{14}}$$

Per the following reason:

It is well known that $$V[m/\sec] = \frac{D\,[m]}{T\,[\sec]}$$

SOS is defined as velocity; BTD is defined as distance and T is defined as time.

here BTD is the bone travel distance, which is determined by the distance between scanning crystals 122 and 124 and angle α.

It is particular feature of ultrasonic apparatus 100 that digital computing device 18 includes a frequency selection mechanism 148, by means of which the User of apparatus 100 may select a frequency at which ultrasonic pulses are to be transmitted by scanning crystal 122, and a full wave quantity selection mechanism 152, by means of which the user of apparatus 100 may select a quantity of full waves to constitute an ultrasonic pulse to be transmitted by scanning crystal 122. Frequency selection mechanism 148 and full wave quantity selection mechanism 152 also receive input from components of digital computing device 18 (full waves quantity counting mechanism 146 and waveform analyzing mechanism 150, as explained below) which can automatically determine the frequency at which ultrasonic pulses are to be transmitted, and the quantity of full waves to constitute each transmitted ultrasonic pulse. Frequency selection mechanism 148 and full wave quantity selection mechanism 152 input the selected frequency and number of full waves into a generator of electrical pulses 140. Generator 140 is a functional generator operative to generate electrical pulses at the frequency defined by frequency selection mechanism 148, and comprising the quantity of full waves defined by full wave quantity selection mechanism 152. The electrical pulses generated by generator 140 are input to wide band scanning crystal 122, resulting in the generation of an ultrasonic signal of the selected frequency and number of waves. The propagated ultrasonic wave passes through soft tissue 16 and bone tissue 14, and is received by scanning ultrasonic crystal 124. The received signal is then input to a first analogue to digital converter 142, which is operative to digitize the waveforms of ultrasound signals received by wide band scanning crystal 124. First analogue to digital converter 142 then inputs the digitized waveform to a first signal waveform memory 144, which is operative to store digitized waveforms of received signals. A full waves quantity counting mechanism 146 then determines the quantity of full waves in the digitized waveform stored in first signal waveform memory 144, and a waveform analyzing mechanism 150 analyzes the stored digitized waveform so as to identify at least two sequential full waves of equal amplitude in the received signal. Waveform analyzing mechanism 150 also determines the serial number, within the sequence of received waves, of the first full wave, that is, the first wave of maximal amplitude within the received signal. Digital computing device 18 is operative to compare the first wave of maximal amplitude, and subsequent waves, within the received signal, with the waves of corresponding serial numbers within the pulse transmitted by scanning crystal 122. Waveform analyzing mechanism 150 also determines differentiation in the zero cross area of the waveform stored in first signal waveform memory 144(dY/dX).

Ultrasonic apparatus 100 functions as follows: The operator applies ultrasonic probe 12 to soft tissue 16 overlying bone tissue 14 under interrogation. An ultrasonic pulse of high frequency (for example, greater than 5 MHz) comprised of four waves is transmitted into bone tissue 14. These initial transmission parameters are determined manually and empirically by the operator. The pulse is repeated at a pulse repetition frequency of approximately 1 kHz. The propagated signal is then received by probe 12, after having passed through bone tissue 14. Full waves quantity counting mechanism 146 counts the number of full waves in the received pulse, and compares this number to the number of full waves in the transmitted pulse. If the received pulse does not contain the same number of full waves (periods) as the transmitted pulse, full waves quantity counting mechanism 146 instructs frequency selection mechanism 148 to decrease the frequency of the transmitted pulse by 0.1 MHz. The pulse transmission and analysis is then repeated until such time as four waves are identified by full waves quantity counting mechanism 146, at which point the transmission frequencies no longer decremented. Waveform analyzing mechanism 150 then analyzes the amplitudes (positive, negative or peak-to-peak) of each full wave in the received signal so as to determine if at least two sequential full waves of equal amplitude are present. Sequential waves are considered to be equal if the difference between them is approximately 1–3% or less. Waveform analyzing mechanism 150 then instructs full wave quantity selection mechanism 152 to incrementally increase the quantity of full waves in the transmitted pulse by one wave at a time, until such time as the received signal comprises a stationary part which contains at least two sequential full waves of equal amplitude to each other. The serial number of the first full wave in the sequence of full waves having equal amplitudes is determined by digital computing device 18, and is compared with the full wave having the same serial number in the transmitted signal, so as to determine the attenuation and/or ultrasound velocity of the transmitted signal. The current transmission frequency is stored, and digital computing device 18 then progressively decreases the frequency of the transmitted pulse until such time as waveform analyzing mechanism 150 detects distortion of the received waveform in the zero cross area (by determining that the differential of the received signal in the zero cross area is equal to zero). The transmission frequency at which this occurs is stored, and digital computing device 18 analyzes the upper and lower frequency limits, as detected, and generates an image of the thickness of bone 14 from the acquired ultrasonic data. Finally, the frequency spectra of the sinusoids constituting all the received signals which had been transmitted within the upper and lower frequency limits are analyzed by digital computing device 18, and, in an iterative process, an image of bone 14 is generated from the acquired ultrasonic data. The generated image or images are then displayed on display 20.

Figure 12:
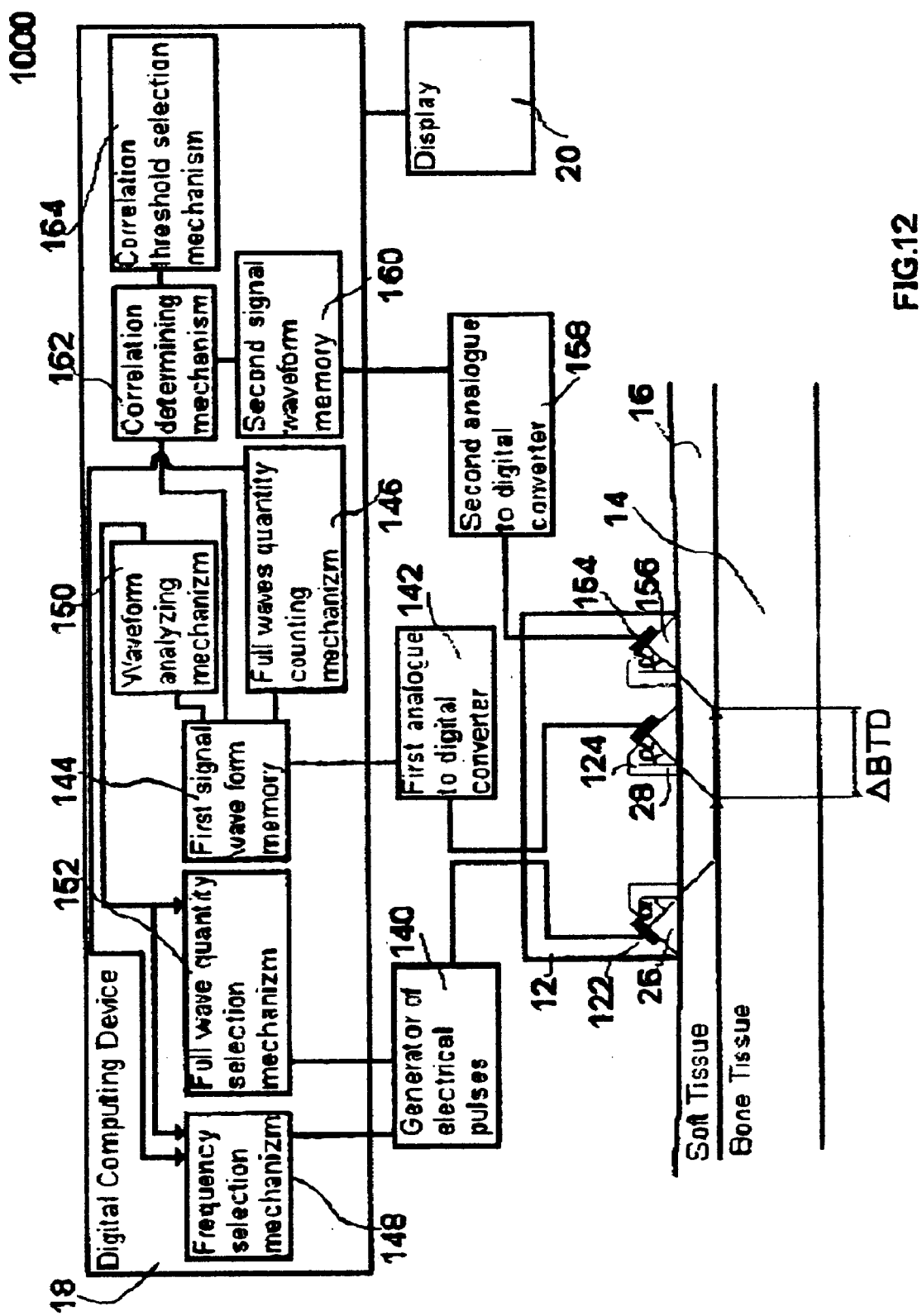
FIG. 12 is a schematic illustration of a second preferred embodiment of an ultrasonic apparatus for imaging bone tissue.

Turning now to FIG. 12, a second preferred embodiment of an ultrasonic apparatus for evaluating bone tissue, generally designated 1000, is schematically depicted. Ultrasonic apparatus 1000 is similar to ultrasonic apparatus 100 and therefore common elements are denoted with the same reference numbers as used to describe ultrasonic apparatus 10 and apparatus 100 above. The components of apparatus 1000 which are designated with the same numbers as referred to above regarding apparatus 100 have identical structure and function to that previously described, such that only the additional elements of apparatus 1000, which do not appear in apparatus 100, will be described.

It is particular feature of ultrasonic apparatus 1000 that ultrasonic probe 12 further includes a third wide band scanning crystal 154 equipped with a delay line 156. Wide band scanning crystal 154 is placed in proximity to receiving wide band scanning crystal 124 (separated by approximately 3 mm), but more distant from transmitting scanning crystal 122 than is receiving scanning crystal 124, and oriented parallel to receiving scanning crystal 124. The distance between wide band scanning crystal 154 and wide band scanning crystal 124 is equal to the difference between the travel distances of ultrasonic signals received by crystals 154 and 124 correspondingly, and is designated ABTD. Delay lines 28 and 156 are identical, thus the ultrasound velocity (SOS) in bone 14 can be calculated by digital computing device 18 using the following formula:

$$SOS = \frac{\Delta BTD}{\Delta T_{14}}$$

Per the following reason:
It is well known that $$V[m/\text{sec}] = \frac{D\ [m]}{T\ [\text{sec}]}$$

SOS is defined as velocity; BTD is defined as distance and T is defined as time.
where ΔT is the time delay between reception of the ultrasonic signal by wide band scanning crystal 154 and by wide band scanning crystal 124.

The addition of third wide band scanning crystal 154 to apparatus 1000 obviates the need to determine propagation times for delay lines 26 and 28 and for soft tissue 16, when calculating the ultrasound velocity in bone tissue 14. As such, the accuracy and repeatability of ultrasonic evaluation of bone tissue is increased.

It is particular feature of ultrasonic apparatus 1000 that it further includes a second analogue to digital converter 158, operative to digitize the waveforms received by third wide band scanning crystal 154. Second analogue to digital converter 158 then outputs the digitized waveforms to a second signal waveform memory 160, which stores the digitized waveforms of signals received by third wide band scanning crystal 154. When ultrasonic probe 12 is oriented optimally with regard to bone tissue 14, the signals received by scanning crystals 124 and 154 will be identical. Thus, a correlation determining mechanism 162 computes a correlation coefficient between the signals stored in memories 144 and 160. A correlation threshold selection mechanism 164 is operative to receive as input from the user a correlation threshold value empirically selected by the user, and to compare that selected value until the correlation coefficient calculated by correlation determining mechanism 162. An example of a typical correlation threshold is 0.95. When the calculated correlation coefficient is above the selected correlation threshold value, digital computing device 18 processes the acquired ultrasonic signals, as described above, so as to generate imaging data for bone tissue 14. However, when the calculated correlation coefficient is below the selected correlation threshold value, digital computing device 18 ceases image processing functions and/or sounds a warning signal alerting the user to the possibility that ultrasonic probe 12 is not optimally applied.

Thus, ultrasonic apparatus 1000 improves the repeatability of results of ultrasonic evaluation of bone tissue by providing real time feedback to the operator regarding the orientation of ultrasonic probe 12 on the patients body. This feedback is based on the ultrasound signals actually received by probe 12 and used for imaging of bone tissue 14.

While the invention has been described with respect to a limited number of embodiments, it will be appreciated that many variations, modifications and other application of the invention may be made.

There has therefore been described a method and device for imaging bone tissue ultrasonically which allows for the precise and easily repeatable measurement of ultrasonic travel time and signal amplitude, the imaging of the internal structure of bone tissue, and the optimization of probe orientation by directly utilizing the imaging signals received from the bone.

What is claimed is:

1. A method for ultrasonic imaging of bone tissue, comprising the steps of
    a) transmitting a repeating ultrasonic signal into the bone tissue, said ultrasonic signal having a frequency and containing a number of full waves;
    b) receiving said transmitted signal;
    c) determining the number of full waves in said received signal;
    d) defining, as a first definition, whether or not said determined number of full waves in said received signal is equal to said number of full waves in said transmitted repeating ultrasonic signal; and
    e) modifying said frequency of said transmitted repeating ultrasonic signal in accordance with said first definition.

2. The method of claim 1, wherein said modifying includes decreasing said frequency of said transmitted repeating ultrasonic signal when said first definition is that said determined number of full waves in said received signal is not equal to said number of full waves in said transmitted repeating ultrasonic signal.

3. The method of claim 1, further comprising the steps of f) determining the amplitude of each full wave in said received signal;

g) defining, as a second definition, whether or not at least two sequential full waves in said received signal are of equal amplitude; and h) modifying said number of full waves in said transmitted repeating ultrasonic signal in accordance with said second definition.

4. The method of claim 3, wherein said modifying in accordance with said second definition includes increasing said number of full waves in said transmitted repeating ultrasonic signal when said second definition is that at least two sequential full waves in said received signal are not of equal amplitude.

5. The method of claim 4, further comprising the steps of i) storing ultrasonic parameters of said received signal when said first definition is that said determined number of full waves in said received signal is equal to said number of full waves in said transmitted repeating ultrasonic signal, and when said second definition is that at least two sequential full waves in said received signal are of equal amplitude; and j) translating said stored parameters into an image of the bone tissue.

6. The method of claim 5, wherein said stored ultrasonic parameters are selected from the group including ultrasound signal velocity, ultrasound signal attenuation, ultrasound signal depth of penetration, and ultrasound signal frequency spectrum.

7. The method of claim 3, further comprising the steps of i) determining the differential in the zero cross area of each full wave in said received signal;

j) defining, as a third definition, whether or not said differential in the zero cross area is equal to zero; and k) modifying said frequency of said transmitted repeating ultrasonic signal in accordance with said third definition.

8. The method of claim 7, wherein said modifying in accordance with said third definition includes decreasing said frequency of said transmitted repeating ultrasonic signal if said third definition is that said determined differential in the zero cross area is not equal to zero.

9. The method of claim 8, further comprising the steps of l) storing a first value for said frequency of said transmitted repeating ultrasonic signal when said first definition is that said determined number of full waves in said received signal is equal to said number of full waves in said transmitted repeating ultrasonic signal;

m) storing a second value for said frequency of said transmitted repeating ultrasonic signal when said third definition is that said determined differential in the zero cross area is equal to zero; and n) calculating a relationship between said stored first and second values.

10. A method for optimizing the orientation of an ultrasound probe on bone tissue, comprising the steps of:

a) transmitting an ultrasound signal into the bone tissue from a transmitter in the ultrasound probe;

b) receiving said transmitted ultrasound signal by a first receiver in the ultrasound probe;

c) receiving said transmitted ultrasound signal by a second receiver in the ultrasound probe, said second receiver being placed at a distance, approximately 3 mm, from said first receiver, in relationship to said transmitter;

d) correlating said ultrasound signal received by said first receiver with said ultrasound signal received by said second receiver, to produce a correlation coefficient;

e) selecting a desired correlation threshold;

f) comparing said produced correlation coefficient to said selected desired correlation threshold; and g) displaying the result of the comparison.

11. A bone tissue ultrasonic imaging system, comprising a) a first wide band scanning crystal for transmitting, an ultrasonic signal into the bone tissue;

b) a frequency selection mechanism for selecting a frequency for said transmitted ultrasonic signal;

c) a full wave quantity selection mechanism for selecting a quantity of full waves for said transmitted ultrasonic signal;

d) a second wide band scanning crystal for receiving said transmitted ultrasonic signal;

e) a full wave quantity counting mechanism for counting a quantity of full waves in said received ultrasonic signal, and inputting to said frequency selection mechanism a desired output frequency;

f) a waveform analyzing mechanism for analyzing waveforms in said received ultrasonic signal, inputting to said frequency selection mechanism a desired output frequency, and inputting to said full wave quantity selection mechanism a desired quantity of full waves for said transmitted ultrasonic signal.

12. A system for optimizing the orientation of a bone ultrasonic imaging probe, comprising a) a first wide band scanning crystal for transmitting an ultrasonic signal into the bone tissue;

b) a second wide band scanning crystal for receiving said transmitted ultrasonic signal;

c) a third wide band scanning crystal for receiving said transmitted ultrasonic signal, said third wide band scanning crystal being placed at a distance, approximately 3 mm, from said second wide band scanning crystal, in relationship to said first wide band scanning crystal;

d) a mechanism for correlating said received ultrasonic signal from said second wide band scanning crystal with said received ultrasonic signal from said third wide band scanning crystal, thus producing a correlation coefficient;

e) a mechanism for selecting a desired correlation threshold;

f) means for comparing said produced correlation coefficient to said selected desired correlation threshold; and g) display of the result of the comparison.

* * * * *

UNITED STATES PATENT AND TRADEMARK OFFICE
CERTIFICATE OF CORRECTION

PATENT NO. : 6,322,507 B1
DATED : November 27, 2001
INVENTOR(S) : Passi et al.

It is certified that error appears in the above-identified patent and that said Letters Patent is hereby corrected as shown below:

<u>Title page,</u>
Please insert in the appropriate place the following text:
Related U.S. Application Data
[60] the date of the US Provisional Application should show Oct <u>26,</u> 1998 not "25"

Signed and Sealed this

Second Day of April, 2002

*Attest:*

JAMES E. ROGAN
*Attesting Officer*     *Director of the United States Patent and Trademark Office*